United States Patent [19]
Kalota et al.

[11] Patent Number: 4,996,369
[45] Date of Patent: Feb. 26, 1991

[54] NOVEL PERFLUORINATED POLYETHERS AND PROCESS FOR THEIR PREPARATION

[75] Inventors: Dennis J. Kalota, Fenton; John S. McConaghy, Jr., St. Louis; Paul W. Foerst; Paul H. Liu, both of Chesterfield, all of Mo.; Frank R. Feher, Jr., Belleville, Ill.

[73] Assignee: Monsanto Company, St. Louis, Mo.

[21] Appl. No.: 498,057

[22] Filed: May 23, 1990

Related U.S. Application Data

[62] Division of Ser. No. 150,963, Jan. 29, 1989.

[51] Int. Cl.$^5$ .............................................. C07C 43/11
[52] U.S. Cl. ................................. 568/615; 252/78.1; 252/52 A; 252/54; 258/240
[58] Field of Search ......................................... 568/615

[56] References Cited

U.S. PATENT DOCUMENTS 4,523,039  6/1985  Lajow et al. .......................... 568/615

Primary Examiner—Howard T. Mars
Attorney, Agent, or Firm—W. Brooks

[57] ABSTRACT

Perfluorinated polyethers having the formula

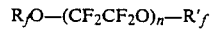

$$R_fO-(CF_2CF_2O)_n-R'_f$$

wherein n is and integer of 1–11 and each of $R_f$ and $R'_f$ is a perfluorinated $C_1$–$C_5$-alkyl radical, dimers of such polyethers and carbon to carbon intramolecularly coupled cyclic derivatives of such polyethers are produced by direct fluorination of the polyethers in an inert solvent. Compositions of the perfluorinated polyethers and their derivatives are useful as functional fluids.

1 Claim, 2 Drawing Sheets

NOVEL PERFLUORINATED POLYETHERS AND PROCESS FOR THEIR PREPARATION

This is a division of patent application Ser. No. 07/150,963, filed Jan. 29, 1989.

BACKGROUND OF THE INVENTION

I Field of the Invention

The present invention relates to new polymeric products of high purity whose molecules consist essentially of carbon, fluorine, and oxygen and having a polyether structure and to a new process for preparing the same by directly fluorinating the corresponding polyether consisting essentially of carbon, hydrogen, and oxygen in a solvent. More particularly, the present invention relates to perfluorinated polyethers consisting of about one to eleven $-(CF_2CF_2O)$ repeating units terminated with perfluorinated $C_1$-$C_5$ alkyl radicals and to a new process for preparing the same by directly fluorinating the corresponding polyether in an inert solvent.

II Description of the Prior Art

Certain organofluoro compounds and polymers are known to exhibit outstanding high temperature stability properties and chemical inertness. Organofluoro compounds containing only carbon and fluorine atoms, fluorocarbon ethers and fluorocarbon amines are three general classes of materials which have found commercial success as coolants, lubricants, heat-transfer agents in reflow condensation soldering processes, and other functional fluid uses. Many compounds can be fully and directly chlorinated or brominated. However, when such compounds are directly fluorinated considerable difficulties are encountered.

Because perfluorinated polyethers have desirable properties, such as extremely good heat stability, outstanding chemical inertness, excellent lubricating properties and the like, much effort has been made to prepare perfluorinated polyethylene oxide having perfluoroalkyl terminal groups. Limited success has been reported in preparing such perfluorinated polymers having a low number (i.e., 2–4) of repeating ethylene oxide units and in preparing such perfluorinated polymers having a high molecular weight. For example, when high molecular polyethylene oxides are perfluorinated, most of the resulting product is a high molecular weight solid with only a small amount of low molecular weight fluid being formed. In order to prepare perfluorinated polyethers of mid-range molecular weights, i.e. being composed of 4–11 perfluoroethylene oxide units, it has been suggested to break solid perfluoro polyethers of high molecular weight into low molecular weight fragments by means of pyrolyzing the perfluoro polyethers at extremely high temperatures of 500–600° C. and collecting the vaporized lower molecular weight perfluoro polyether fluids. The pyrolysis is not only expensive and difficult to carry out but also the resulting fluids are random mixtures of many perfluoro polyethers because of the random nature of the bond breakage of the high molecular weight perfluoro polyethers. The fragments must be reacted with fluorine gas to eliminate acyl end groups and any unsaturation of the resulting perfluoro polyethers.

Efforts to provide a process for the direct fluorination of organic compounds in solvents have heretofore been fraught with many problems, including the breakdown of the solvent by the fluorine gas, formation of explosive mixtures, and the insolubility of the fluorine gas with the solvent.

SUMMARY OF THE PRESENT INVENTION

The present invention provides a process for direct and full fluorination of linear polyethylene oxide ethers in a solvent. The perfluorinated polyethylene oxide ethers are characterized by the formula

$$R_fO-(CF_2CF_2O)_n-R'_f$$

wherein n is an integer from 1–11 and include dimers and cyclic compounds thereof resulting from intramolecular carbon to carbon coupling. The $R_f$ and $R'_f$ radicals which may be the same or different radicals are perfluorinated $C_1$-$C_5$ alkyls, including perfluoromethyl, perfluoroethyl, perfluoropropyl, perfluoroisopropyl, perfluorobutyl, perfluoroisobutyl, and perfluoro-t-butyl. The preferred perfluorinated polyethylene oxides have a molecular weight of about 250-2000 and boil above 130° C.

In accordance with the process aspect of the present invention a polyether having the following formula is produced by conventional procedures

$$RO-(CH_2CH_2O)_n-R'$$

wherein n is an integer of 1–11 and preferably an integer of 5–8. Each of R and R' is a $C_1$-$C_5$ alkyl radical independently selected from methyl, ethyl, propyl, isopropyl, butyl, isobutyl, t-butyl, etc. The polyether is dissolved in a suitable chemically inert fluorocarbon fluid. The preferred solvent is 1,1,2-trichloro-1,2,2-trifluoroethane. The solvent should not only be chemically inert in respect to reactants and products, it should also be free of contaminants, such as iron and nickel fluorides that would catalyze a reaction between the fluorine gas and the solvent resulting in the decomposition of the solvent. Gaseous fluorine is introduced into the solvent containing the polyether dissolved therein to provide intimate contact between the fluorine of suitably small bubble size and the polymer while the solvent is vigorously being agitated. Fluorine gas may be brought into the reaction alone or together with an inert gas. Preferably, during the initial stages of the reaction the concentration of the fluorine is maintained at a relatively low level to control the rapidity of the fluorination. As the reaction proceeds, the concentration of the fluorine gas may be increased. Since hydrogen fluoride (HF) is produced as a by-product and gives rise to HF handling problems and polyether decomposition, fluorination of the polyethers can be advantageously carried out in the presence of a HF scavenger, such as sodium fluoride and potassium fluoride. The scavenger is not ordinarily soluble in the fluorocarbon fluid and is slurried in the solvent as a powder or other comminuted particles. Although it is important that a scavenger be used since it will react with the by-product hydrogen fluoride to minimize the reactive presence thereof, it is not essential to the carrying out of the process of the present invention.

Since direct fluorination reactions are highly exothermic, care is taken to adequately cool the reactants while the reaction is occurring. Direct fluorination of the polyethers in an inert solvent can take place in a variety of corrosion resistant reactors, such as rotating drum reactors, stirred autoclaves, and the like.

Care must be taken in the selection of the material of construction of the container in which the reaction takes place such that the container or its products of corrosion do not provide for the presence of any compound that would initiate or catalyze an adverse reaction resulting in excessive decomposition of the solvent.

One material for making a suitable reaction vessel is a nickel-molybdenum-chromium wrought metal alloy which exhibits resistance to the process environment of the present invention and does not provide a source of contaminants that would initiate or catalyze decomposition of the inert solvent. A preferred corrosion-resistant alloy is one composed of more than fifty percent of nickel, about 15% of molybdenum, about 15% of chromium, together with minor amounts of other metals such as Co, W, Fe, Si and Mn. One suitable alloy is sold as Hastelloy alloy C-276.

Finally, the perfluorinated polyethers are separated from the reaction mixture.

The present invention provides the advantages of producing perfluoro polyethers by a direct fluorination process and of significant reduction of reaction time by using a solvent reaction medium. While direct fluorination processes are known, carrying out such process using a solvent for both the polyether and the perfluorinated polyether reaction process has not heretofore been successful. Another advantage of the present invention is that perfluorinated polyethers of a molecular weight range of about 250 to 2000 are conveniently provided in a direct manner rather than by cleaving perfluorinated polyethers of high molecular weights.

The novel perfluorinated polyethers, dimers thereof, cyclic compounds thereof resulting from intramolecular carbon to carbon coupling, and mixtures thereof, alone or dissolved in a solvent as herein disclosed are useful as functional fluids, including lubricants, vacuum pump oils, and heat exchange agents. Perfluorinated polyethers boiling in the range of about 130–330° C. are especially useful in vapor phase soldering applications.

DETAILED DESCRIPTION OF THE INVENTION

Figure 1:
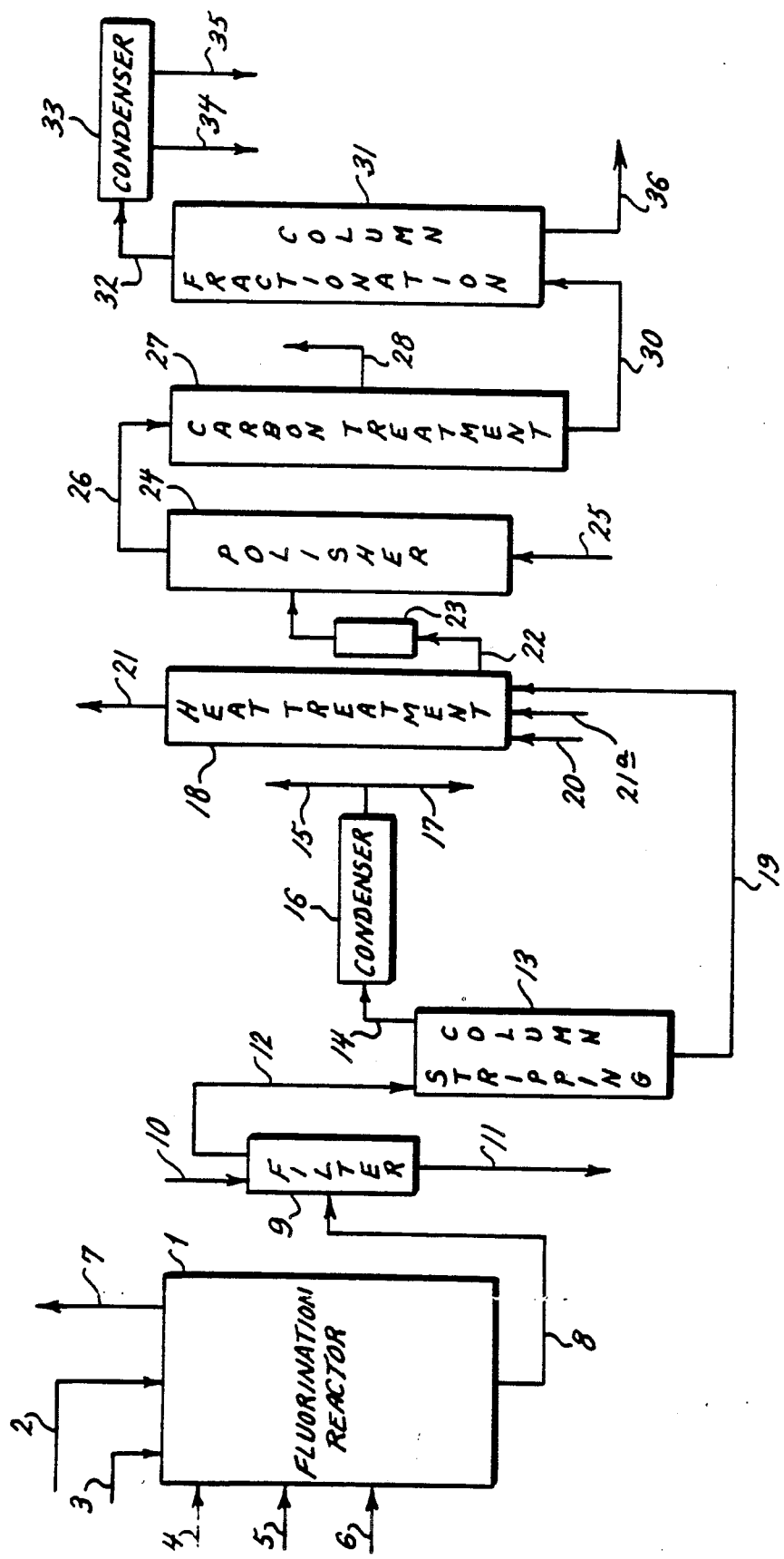
FIG. 1 is a schematic block diagram showing one form of apparatus useful for practicing the invention.

The present invention provides the manufacture of useful perfluorinated polyethers having a molecular weight range of about 250-2000, many of which are believed to be novel, and the manufacture of certain useful dimers of perfluorinated polyethers, and the manufacture of cyclic compounds thereof resulting from intramolecular carbon to carbon coupling, which are also believed to be novel. The perfluoropolyethers of the present invention can be represented by the following abbreviated formula $$R_fO-(CF_2CF_2O)_n-R'_f$$

In this formula n represents an integer of about 1–11 and each of $R_f$ and $R'_f$ is independently selected from perfluorinated $C_1-C_5$ alkyl radicals including perfluoromethyl, perfluoroethyl, perfluoropropyl, perfluoroisopropyl, perfluorobutyl, perfluoroisobutyl, and perfluoro-t-butyl. Preferred $R_f$ and $R'_f$ radicals are perfluoromethyls. The perfluorinated polyethers also may be carbon to carbon intramolecularly coupled cyclic derivatives of the just-mentioned linear perfluorinated polyethers. Cyclic derivatives are represented by the formulas

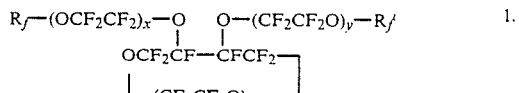 1.

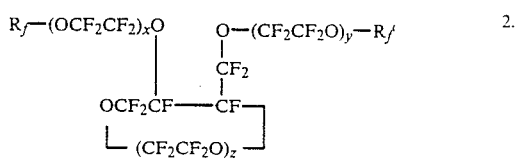 2.

 3.

wherein $R_f$ and $R'_f$ are as above described; $R''_f$ and $R'''_f$ are perfluoroalkylene groups corresponding to R 5 and $R'_f$; w=3 to 11, inclusive, and x+y+z=1 to 9, inclusive.

Commonly, perfluoromethyl polyethylene oxides are known as perfluoropolyglymes. This term does not precisely follow an officially recognized chemical nomenclature system but is based on glymes being used to refer to polyethylene glycols terminated with methyl groups. On this basis $CH_3O-(CH_2CH_2O)_6-CH_3$ is named hexaglyme and $CH_3O-(CH_2CH_2O)_7-CH_3$ is named heptaglyme. When heptaglyme is fully fluorinated, the resulting product is known as perfluoroheptaglyme and has the formula $CF_3O-(CF_2CF_2O)_7-CF_3$, and may be abbreviated PFHG. More properly, PFHG can be named 1,1,1,3,3,4,4,6,6,7,7,9,9,10,10,12,12,13,13,15,15,16, 16,18,18,19,19,21,21,22,22,24,24,24-tetratriacontafluoro-2, 5,8,11,14,17,20,23-octaoxatetracosane. This compound and compositions containing the compound in a solvent therefore are new and are useful as functional fluids, such as lubricants and heat transfer agents.

In addition to PFHG other perfluoroethylene glycol ethers include perfluorotriglyme, perfluorotetraglyme, perfluoropentaglyme, perfluorohexaglyme, perfluorooctaglyme, perfluorononaglyme, perfluorodecaglyme, perfluoroundecaglyme, etc. Instead of being terminated with two perfluoromethyls, the same perfluorinated polyethylene glycol backbone can be terminated (i.e. $R_f$ and $R'_f$) with perfluoroethyl, perfluoropropyl, perfluoroisopropyl, perfluorobutyl, perfluoroisobutyl, perfluoro-t-butyl, etc. The $R_f$ and $R'_f$ radicals may be the same or different.

The present invention also provides for the production of an isomeric mixture of dimers of PFHG. Such dimers are given the common name of diperfluoroheptaglyme or more properly hexahexacontafluorohexadecaoxadotricontane. The diperfluoroheptaglyme isomers can be represented by the following formulas

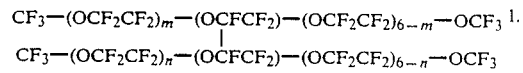

where m and n may vary from 0—6

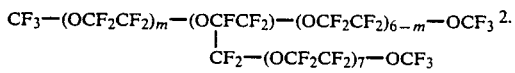 2.

where m may vary from 0–6.

 3.

In the direct fluorination of heptaglyme dimers thereof are produced via radical coupling reaction. The carbon to carbon radical coupling that produces the dimers may occur two or more times generating cyclic perfluoropolyethers of corresponding longer chains. The additional couplings may occur in an end to end arrangement or between sets of ethylene carbons. The following structure represents an example os such coupled dimers but does not include all possible structures since cross linking may occur at either of the ethylene carbons

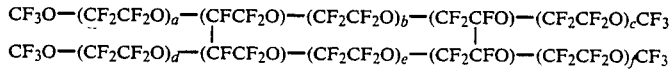

wherein $a+b+c+d+e+f=0$ to 12, inclusive.

The direct fluorination of polyethers to produce PFHG monomer and dimers by the present process can be depicted by the following equation

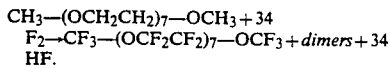

Where a HF scavenger, for example sodium fluoride, is used to obviate the problems of handling hydrogen fluoride, the process can be depicted by the following reaction

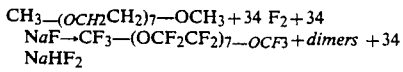

The reaction of perfluorination of polyethers is very exothermic. For example, the heat of reaction of preparing PFHG in accordance with the present invention is 4427 kcal/mol of heptaglyme. This means that to minimize the formation of unwanted reaction products, the reaction medium should normally be positively cooled by the use of heat exchangers or the like.

In one preferred embodiment of the present invention, a reactor constructed of a suitable metal alloy, such as Hastelloy-C is charged with heptaglyme or other suitable precursor polyether and a slurry of sodium fluoride scavenger and an inert solvent for the polyether. As indicated above the preferred solvent is 1,1,2-trifluoro-1,2,2-trifluoroethane. Other suitable solvents may likewise be employed. The resulting mixture is vigorously agitated. The air in the reactor is purged with nitrogen to remove oxygen which may interfere with the reaction resulting in unwanted by-products. The reactor mixture is maintained at a desirably low temperature. The fluorine gas is bubbled below the level of the solvent containing the polyether at a point of significant agitation. The fluorine is initially diluted with nitrogen with the concentration of the nitrogen being reduced and the concentration of the fluorine correspondingly increased. Fluorination continues until fluorine no longer is consumed but breaks through the reaction mixture unreacted at which time the need for cooling is reduced. The reaction mass is filtered to remove sodium fluoride and sodium bifluoride. The solvent is then separated by a conventional operation, such as distillation. At this point the fluorination of the polyether may be only about 90% complete. To complete the fluorination the partially fluorinated polyether with or without HF scavenger is heated in the presence of fluorine gas at an elevated temperature, for example up to about 150° C. At this point the fluorinated polyether may contain some acyl fluoride end groups. These end groups are preferably eliminated by polishing the products at elevated temperatures of 150–250° C. or higher and pressures of up to 300 psig or higher in the presence of fluorine for a sufficient length of time.

Instead of completing the fluorination and acyl end group conversion in separate steps, both chemical conversions can be carried out in a single operation. In a single operation increased degradation of reactants to undesired products is more likely to be experienced.

Preferred HF scavengers include alkali metal fluoride, more preferably sodium fluoride or potassium fluoride. Calcium carbonate, sodium monofluorophosphate, alkali metal fluorophosphate, etc. may also be used as useful HF scavengers.

Figure 2:
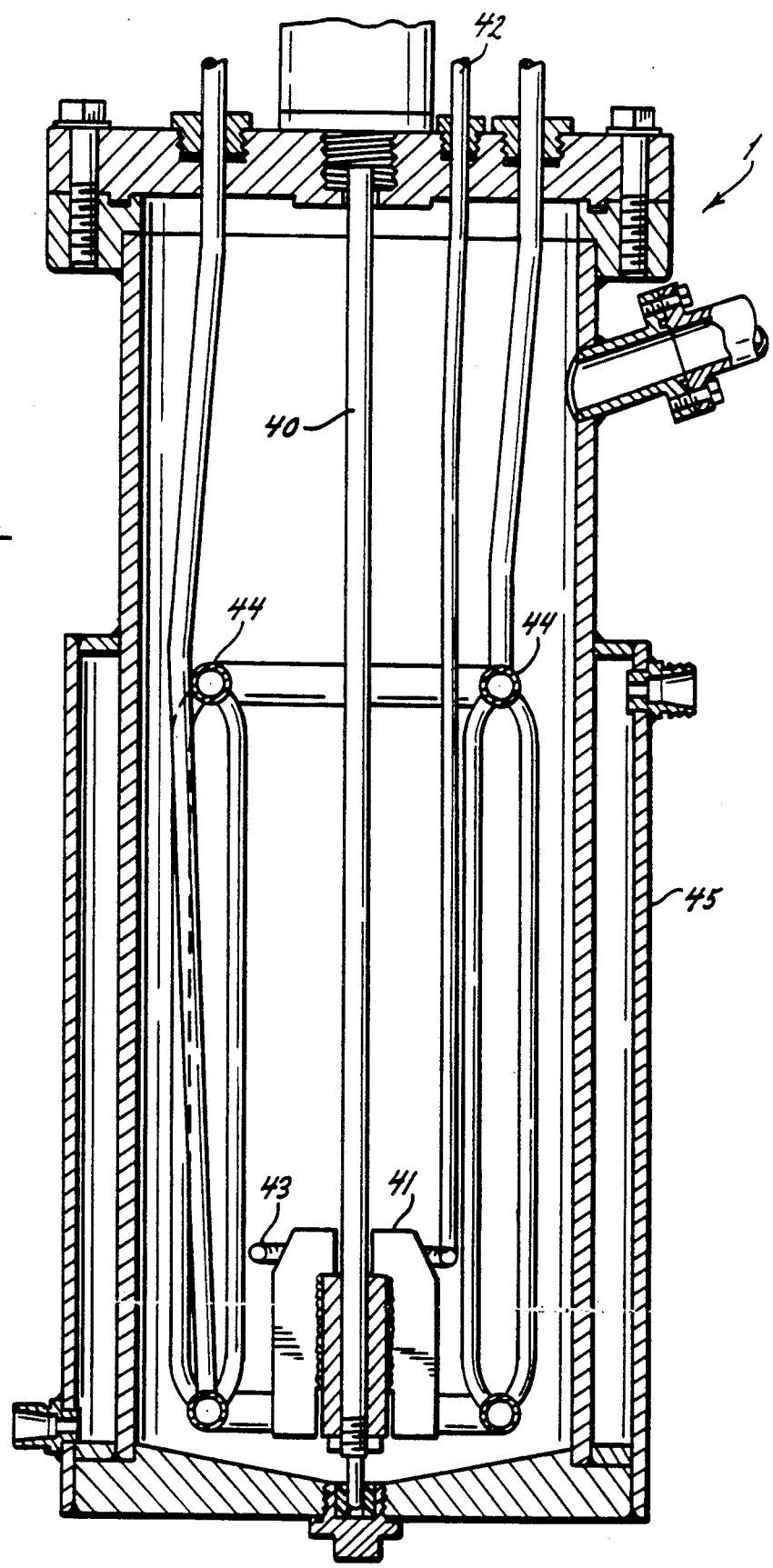
FIG. 2 is a cross section elevational view of a reactor for conveniently carrying out the fluorination of polyethers in accordance with the present invention.

With reference now to FIG. 1 of the attached drawing numeral 1 denotes a fluorination reactor whose structure is given in more detail in FIG. 2. Solvent is supplied to the reactor 1 via line 2 from a suitable source of solvent. Polyether is supplied to reactor 1 via line 3 from a suitable source of polyether. A HF scavenger is supplied to reactor 1 via line 4 from a suitable source of scavenger. Fluorine gas is supplied to reactor 1 via line 5 from a suitable source of fluorine gas. Nitrogen or other suitable inert gas is supplied to reactor 1 via line 6 from a suitable source of inert gas.

In operation, reactor 1 is charged with polyether, solvent and optionally HF scavenger; and high speed agitation is begun. Air is purged from the reactor with nitrogen or other inert gas. This is done to remove oxygen which might interfere with the reaction by adding oxygen to the organic radicals that are generated causing a reduced fluorine uptake. Otherwise, there would be produced a contaminated product. The reaction temperature is reduced and controlled by employing an efficient internal cooling coil or the like. During fluorination the generated heat of reaction is significant and is removed. Fluorine is introduced at a point near where an effective agitating means is located. In the initial stages of the reaction fluorine is normally diluted with nitrogen or other inert gas. When the reaction nears completion, fluorine is emitted in rapidly increasing quantities as an off gas and leaves reactor 1 via line 7 and passes through an off gas monitoring device not shown, wherein fluorine is converted to oxygen and the oxygen concentration is measured. By-product HF is reacted with the scavenger, if one is used. When breakthrough of the flourine gas is detected, the reaction is discontinued. At this stage the polyether may have about 90% of its hydrogens exchanged for fluorines.

The reaction mass is passed via line 8 through a filter 9 to remove solid products resulting from the use of the scavenger. The solids may be washed with solvent supplied via line 10 and then removed through line 11. After filtration, the liquid partially fluorinated polyether is pumped through line 12 to a stripper column 13, wherein the solvent and entrained gases are stripped overhead. The gases are removed via line 15. The solvent is condensed by condenser 16 and may be returned to the system for reuse via line 17.

Heat treatment of the reaction mass is completed in a heat treatment reactor 18 to provide the exchange of any residual hydrogens with fluorines to produce a perfluorinated oil. The partially fluorinated polyether is pumped from column 13 to reactor 18 via line 19. Fluorine gas is introduced into reactor 18 through a line 20 from a suitable source. Exchange of remaining hydrogens with fluorine may require the use of elevated temperatures. In the early stages of heat treatment residual solvent may be flashed and removed from the reactor 18 via line 21.

Reactor 18 is preferably equipped with agitation and heating means. The reactor is preferably constructed of Ni—Mo—Cr metal alloy as described more particularly above. HF scavengers may be added to reactor 18 during heat treatment via line 21a, if desired. The heat treated product leaves reactor 18 via line 22. When a HF scavenger is used during the heat treatment, the product is passed through a filter 23 to remove the solids from the liquid stream. Next, the heat treated product is passed through a polishing reactor 24 wherein any terminal acyl fluoride groups of the perfluorinated polyether are eliminated. This polishing is accomplished by heating the product at a temperature and pressure greater than that employed during the heat treatment in reactor 18 and in the presence of fluorine supplied to reactor 24 via line 25. The polished perfluoropolyester preferably is next subjected to a carbon treatment in a vessel 27. Gaseous products resulting from the carbon treatment are vented from the system via line 28. From the carbon treatment the perfluropolyester is moved via line 30 to a fractionation column 31, wherein the desired perfluoropolyether is separated via line 32 from the remaining heavy oil. In condenser 33 the desired perfluoropolyether is condensed and is removed via line 34. Lower boiling perfluoropolyethers are removed via line 35. The high boilers composed mainly of perfluoropolyether dimers are removed via line 36. The yield of perfluoropolyether may be 90% or higher of theoretical with a 70% perfluoropolyether monomer and 30% perfluoropolyether dimer ratio resulting.

With reference now to FIG. 2 there is shown a flourination reactor suitable for carrying out the invention. The reactor generally denoted by numeral 1 is equipped with a high speed stirrer 40 having a blade 41 to effect efficient gas-liquid interfacing. High speeds of above 800 rpm, preferably 1200–1400 rpm, are used due to the relatively low solubility of fluorine in the reaction medium. The fluorine/nitrogen feed gas is introduced into the reactor through conduit 42 and is emitted through fine holes circumferentially disposed in a ring conduit 43 located around the top tapered portion of the stirrer blade. Instead of a ring conduit, gas may be emitted through other gas dispersion equipment, such as porous metal frits. Preferably, there are produced fine gas bubbles less than about 10 microns in diameter when the gas is injected into the reaction mass. This small bubble size aids in maintaining a high fluorine re action rate in the solvent of low fluorine solubility. With the mechanical action of the high speed agitation blade and together with the small gas bubbles a satisfactory high reaction rate can be maintained.

Direct fluorination of polyethers is very exothermic and therefore generates substantial amounts of heat. For example, the direct fluorination of heptaglyme in the presence of sodium fluoride as a hydrogen fluoride scavenger produces 4427 kcal/mole of heptaglyme reacted. To complete the reaction with a high degree of productivity and low by-product formation a high surface area internal heat exchanger 44 is used to provide a high coolant flow. The exchanger also may serve as a baffle for mixing enhancement. The heat of reaction is removed and the reaction temperature is controlled by this internal heat exchanger. As illustrated, the reactor may also be provided with a jacket 45 for additional heat removal by means of a coolant flowing through the jacket. The rapid transfer of heat from the reactants, the high speed agitation of the reactants, and the use of an inert solvent provides for fluorine addition rate several times, at least 3–5 times, the rates that which are typically obtained in known direct fluorination techniques.

The following example describes a preferred embodiment of the invention. Other embodiments within the scope of the claims herein will be apparent to one skilled in the art from consideration of the specification of practice of the invention as disclosed herein. It is intended that the specification, together with the example, be considered exemplary only with the scope and spirit of the invention being indicated by the claims which follow the example. Specifically, in the following examples the improvement in manufacturing PFHG and its dimers has been demonstrated. The method employed to produce such substances can also obviously be used to produce similar perfluorinated polyethers from corresponding polyethers.

Thus, included in the process of the present invention are the compounds: perfluorinated glyme, perfluorinated diglyme, perfluorinated triglyme, perfluroinated tetraglyme, perfluorinated pentaglyme, perfluorinated pentaethylene glycol methylethyl ether, perfluorinated pentaethylene glycol diethyl ether, perfluorinated hexaglyme, perfluorinated hexaethylene glycol methylethyl ether, perfluorinated hexaethylene glycol diethyl ether, perfluorinated heptaglyme, perfluorinated heptaethylene glycol methyethyl ether, perfluorinated heptaethylene glycol diethyl ether, perfluorinated octaglyme, perfluorinated octaethylene glycol methylethyl ether, perfluorinated octaethylene glycol diethyl ether, perfluorinated nonaglyme, perfluorinated nonaethylene glycol methylethyl ether, perfluorinated nonaethylene glycol dimethyl ether, perfluorinated decaglyme, perfluorinated decaethylene glycol methylethyl ether, perfluorinated decaethylene glycol diethyl ether, perfluorinated undecaglyme, dimers thereof and intramolecular carbon to carbon coupled cyclic derivatives of both the monomers and dimers.

In the example all weights are given on a weight basis unless otherwise indicated.

EXAMPLE

A five liter reactor was charged with 250 gm of heptaglyme and a slurry of 1,110 gm of sodium fluoride in 4 liters of 1,1,2-trichloro-1,2,2-trifluoroethane (Freon-113). The reactor was constructed of Hastelloy alloy C-276 having a chemical composition of about 60% Ni, 15% Mo, 14.5% Cr, 3.0% W, 2.5% Co, 4.0% Fe and minor amounts of Si, Mn, C, V, p and S. Stirring was begun and maintained during the reaction at 1200 rpm. Air was purged from the reactor with nitrogen. By means of circulating coolant, the reaction mass temperature was reduced to 15° C. Thereupon, small bubbles of fluorine were introduced into the reactor using a multiported ring positioned around the top of the stirrer blade as illustrated in FIG. 2. The fluorine was initially diluted with nitrogen; the flows of fluorine and nitrogen were adjusted during the reaction as indicated in the following table.

TABLE 1

REACTION PROFILE

| Elapsed Time, Min | Fluorine, sccm | Nitrogen, sccm | Temp., °C. |
|---|---|---|---|
| 0 | 500 | 1000 | 15 |
| 10 | 1000 | 1000 | 15 |
| 20 | 1500 | 500 | 15 |
| 30 | 2000 | 500 | 15 |
| 45 | 2500 | 500 | 15 |
| 245 | 1000 | 500 | 25 |
| 255 | 500 | 500 | 25 |
| 280 | 0 | 1000 | 25 |

Total time until fluorine breakthrough was approximately four hours. Breakthrough was determined by detecting a decreased need for cooling to maintain the desired reaction temperature. A sharp increase in the amount of unreacted fluorine leaving the reactor was determined by following the percent of oxygen in the off gas. This also signaled breakthrough of the fluorine. The reaction off gas passed through an alumina trap reactive with fluorine to produce the oxygen. By determining the amount of oxygen displaced by the fluorine, one is able to determine quantitatively the amount of fluorine being passed through. As the breakthrough occurred, fluorination at a reduced rate was continued for an additional 35 minutes; and the reaction temperature was raised to about 25° C. Thereafter the fluorine feed was discontinued. The reaction mass was agitated for an additional 15 minute period with a nitrogen purge to eliminate any dissolved fluorine. The heptaglyme at this stage had 90-95% of its hydrogens exchanged with fluorines. The fluorine usage in the reaction step was about 110% of theoretical. The reaction mass was filtered and the solvent was stripped from the oil by distillation to provide 634 g of fluorinated oil.

Masses of several fluorination reactions were combined for feed to the subsequent process steps.

A five-liter heat treatment vessel was charged with 7105 g of the fluorinated PFHG oil and 300 g of sodium fluoride. Air was purged from the reactor with nitrogen. The 5-10% remaining hydrogens on the substantially fluorinated heptaglyme were exchanged for fluorines by reacting the crude oil with fluorine at a temperature in the range of 31-128° C. at atmospheric pressure and with vigorous agitation. The flow rates of fluorine and nitrogen were adjusted during the reaction as indicated in Table 2 which follows.

The mixture was filtered affording 6676 g oil. The solids were washed with solvent. The solvent was removed affording an additional 209 g of oil. A second washing with solvent afforded an additional 116 g of oil. A total of 7001 g (95% of charge) of oil was recovered.

TABLE 2

REACTION PROFILE

| Elapsed Time, Min | Fluorine, sccm | Nitrogen, sccm | Temp. °C. |
|---|---|---|---|
| 0 | 500 | 1000 | 31 |
| 10 | 1000 | 1000 | 59 |
| 15 | 1000 | 500 | 70 |
| 20 | 1500 | 250 | 86 |
| 30 | 1500 | 250 | 108 |
| 45 | 2000 | 250 | 113 |
| 60 | 2500 | 250 | 118 |
| 80 | 3000 | 250 | 128 |
| 132 | 2000 | 250 | 127 |
| 137 | 1000 | 250 | 120 |
| 155 | 1500 | 250 | 113 |
| 168 | 1500 | 0 | 113 |
| 177 | 0 | 0 | 112 |

Final polishing was accomplished as follows.

A two liter polishing vessel was charged with 1564 g of heat treated product. The product was stirred at 300 rpm and brought into reactive contact with fluorine. The flow rates of fluorine and nitrogen and the temperature and pressure of the autoclave were adjusted during the reaction as indicated in the following table.

TABLE 3

REACTION PROFILE

| Elapsed Time, Min | Fluorine, sccm | Nitrogen, sccm | Temp., °C. | Press psig |
|---|---|---|---|---|
| 0 | 0 | 15 | 29 | 0 |
| 69 | 20 | 15 | 125 | 0 |
| 71 | 100 | 0 | 130 | 0 |
| 80 | 200 | 0 | 155 | 0 |
| 95 | 200 | 0 | 165 | 0 |
| 143 | 0 | 0 | 236 | 95 |
| 170 | 0 | 0 | 250 | 90 |
| 230 | 0 | 0 | 253 | 90 |

A total of 1505 g (96% of charge) of polished oil was recovered from the reactor.

The thus polished product was refined by distillation to yield a PFHG overhead product and a PFHG dimers bottoms product.

Heat treatment and polishing of the recovered oil, respectively, completed the exchange of residual hydrogens with fluorines and eliminated acyl fluoride groups generated by cracking.

The following properties of PFHG and dimmers were measured and have been set forth in the following table.

TABLE 4

| PFHG | |
|---|---|
| Average Molecular Weight | 1000 |
| Boiling Point, °C. @ 760 torr | 215 |
| Pour Point, °C. | −25 |
| Density @ 25° C. g/cc | 1.72 |
| PFGH DIMERS | |
| Average Molecular Weight | 1900 |
| Boiling Point, °C. @ 4 torr | 200 |
| Pour Point, °C. | −70 |
| Density @ 20° C. g/cc | 1.81 |

EXAMPLE 2

In this example the crude oil of Example 1 from which the solvent had been stripped was heat treated and polished in one reactor without the use of sodium fluoride scavenger or any other HF scavenger. A two-liter autoclave reactor was charged with 1967 g of the oil. The oil was stirred at 1000 rpm and brought into reactive contact with fluorine. The flows of fluorine and nitrogen and the temperature and pressure of the reactor were adjusted during the reaction as indicated in the following table.

TABLE 5

REACTION PROFILE

| Elapsed Time, Min. | Fluorine, sccm | Nitrogen, sccm | Temp., °C. | Press., psig. |
|---|---|---|---|---|
| 0 | 0 | 50 | 24 | 0 |
| 31 | 50 | 15 | 50 | 0 |
| 50 | 200 | 15 | 70 | 0 |
| 75 | 400 | 15 | 100 | 0 |
| 365 | 50 | 0 | 128 | 0 |
| 380 | 200 | 0 | 137 | 0 |

TABLE 5-continued

REACTION PROFILE

| Elapsed Time, Min. | Fluorine, sccm | Nitrogen, sccm | Temp., °C. | Press., psig. |
|---|---|---|---|---|
| 415 | 0 | 0 | 157 | 80 |
| The reactor was cooled for sampling. | | | | |
| 0 | 200 | 0 | 31 | 0 |
| 33 | 0 | 0 | 35 | 80 |
| 153 | 0 | 0 | 249 | 90 |
| 213 | 0 | 0 | 250 | 90 |
| The reactor was cooled for sampling. | | | | |
| 0 | 200 | 0 | 85 | 0 |
| 27 | 0 | 0 | 109 | 80 |
| 96 | 0 | 0 | 250 | 112 |
| 156 | 0 | 0 | 251 | 112 |

A total of 1884 g (96% of charge) of polished oil was recovered.

What is claimed is:

1. Perfluoroheptaglyme dimer.

* * * * *